(12) United States Patent
Tai et al.

(10) Patent No.: US 6,994,950 B2
(45) Date of Patent: Feb. 7, 2006

(54) METHOD FOR INTEGRATING MICRO- AND NANOPARTICLES INTO MEMS AND APPARATUS INCLUDING THE SAME

(75) Inventors: Yu-Chong Tai, Pasadena, CA (US); Qing He, Pasadena, CA (US)

(73) Assignee: California Institute of Technology, Padadena, CA (US)

( * ) Notice: Subject to any disclaimer, the term of this patent is extended or adjusted under 35 U.S.C. 154(b) by 261 days.

(21) Appl. No.: 10/391,122

(22) Filed: Mar. 18, 2003

(65) Prior Publication Data

US 2003/0228411 A1    Dec. 11, 2003

Related U.S. Application Data

(60) Provisional application No. 60/366,019, filed on Mar. 19, 2002.

(51) Int. Cl.
*G03F 7/00* (2006.01)

(52) U.S. Cl. .............. 430/320; 430/311; 430/313; 430/315; 430/319; 430/329
(58) Field of Classification Search .......... 430/311, 430/313, 315, 319, 320, 329
See application file for complete search history.

(56) References Cited

U.S. PATENT DOCUMENTS

| | | | |
|---|---|---|---|
| 5,364,497 A | * | 11/1994 | Chau et al. ............ 216/39 |
| 5,374,449 A | | 12/1994 | Buhlmann et al. ...... 427/100 |
| 5,474,808 A | | 12/1995 | Aslam ................ 427/249.9 |
| 5,600,197 A | | 2/1997 | Takeuchi et al. ........ 310/328 |
| 5,679,436 A | * | 10/1997 | Zhao ................... 428/141 |
| 6,046,659 A | | 4/2000 | Loo et al. ............. 333/262 |
| 6,478,974 B1 | | 11/2002 | Lebouitz et al. .......... 216/2 |
| 2002/0020053 A1 | | 2/2002 | Fonash et al. ......... 427/100 |

* cited by examiner

*Primary Examiner*—Nicole Barreca
(74) *Attorney, Agent, or Firm*—Foley & Lardner LLP

(57) ABSTRACT

MEMs devices are integrally fabricated with included micro or nanoparticles by providing a mixture of a sacrificial material and a multiplicity of particles, disposing the mixture onto a substrate, fabricating a MEMs structure on the substrate including at least part of the mixture, so that at least some of the mixture is enclosed in the MEMs structure, removing the sacrificial material, and leaving at least some of the multiplicity of particles substantially free and enclosed in the MEMs structure. The step of fabricating a MEMs structure is quite general and is contemplated as including one or a multiplicity of additional steps for creating some type of structure in which the particles, which may be microbeads or nanobeads, are included. A wide variety of useful applications for MEMs integrated with micro or nanoparticles are available.

25 Claims, 4 Drawing Sheets

METHOD FOR INTEGRATING MICRO- AND NANOPARTICLES INTO MEMS AND APPARATUS INCLUDING THE SAME

RELATED APPLICATIONS

The present application is related to U.S. Provisional Patent Application Ser. No. 60/366,019, filed on Mar. 19, 2002, which is incorporated herein by reference and to which priority is claimed pursuant to 35 USC 119.

The U.S. Government has certain rights in the invention pursuant to Grant No. 5R01 RR06217–08 awarded by the National Institute of Health.

BACKGROUND OF THE INVENTION

1. Field of the Invention

The invention relates to the field of micro-electro-mechanical systems (MEMS) and in particular to the use of micro and nanobeads in MEMS.

2. Description of the Prior Art

There has been a great deal of interest in integrating special micro-scale particles on a chip, especially in micro-electro-mechanical systems (MEMS). There are already many applications of microparticles in MEMS and even more are expected once particles can be easily integrated and localized. Fluorescent and dyed particles are frequently used in microfluidic devices for flow visualization. Magnetic microbeads can be manipulated in micro devices for future transportation of chemical reagents and cells. One-time microvalves and micropumps have been demonstrated using expandable microspheres. Pressures in excess of 8000 psi have been achieved using silica beads packed capillaries. Special microspheres have been demonstrated for multianalyte sensor arrays for the analysis of complex fluids containing a variety of important classes of analytes.

However, none of these applications directly integrates particles into the subject system. Instead, the particles are usually injected through access holes or placed by micromanipulators after device fabrication. Since these are not batch processes and have to be done die by die, it is impractical and cost-ineffective to make integrated miniaturized systems. Hence, an easy, inexpensive, batch process is needed. The invention satisfies these requirements.

BRIEF SUMMARY OF THE INVENTION

The invention is a method for fabricating MEMs devices comprising the steps of providing a mixture of a sacrificial material and a multiplicity of particles, disposing the mixture onto a substrate, fabricating a MEMs structure on the substrate including at least part of the mixture, so that at least some of the mixture is enclosed in the MEMs structure, removing the sacrificial material, and leaving at least some of the multiplicity of particles substantially free and enclosed in the MEMs structure. The step of fabricating a MEMs structure is quite general and is contemplated as including one or a multiplicity of additional steps for creating some type of structure in which the particles, which may be microbeads or nanobeads, are included.

In one embodiment of the step of fabricating a MEMs structure on the substrate including at least part of the mixture comprises photolithographically patterning the mixture. Instead of photolithographically patterning the step of fabricating a MEMs structure on the substrate including at least part of the mixture may comprise patterning the mixture by etching the mixture.

The step of providing a mixture of a sacrificial material and a multiplicity of particles comprises providing a mixture of variable viscosity, wherein the viscosity is determined by particle concentration.

In one embodiment the step of providing a mixture of a sacrificial material and a multiplicity of particles comprises providing microspheres in a soluble material. For example, the microspheres can be provided in a mixture with photoresist which is then spin coated onto the substrate. The step of spin coating the mixture onto the substrate further comprises controlling the thickness of the coating by varying the concentration of particles in the mixture.

Since the particles may prevent full exposure of the photoresist, where the sacrificial layer is made from photoresist, the step of fabricating a MEMs structure on the substrate comprises repeatedly photolithographically exposing and etching the mixture, or alternatively the sacrificial material may be reactive ion etched or plasma etched.

The step of removing the sacrificial material comprises defining openings in the MEMs structure to allow entry of an etchant of the sacrificial material and opening at least one filter into an enclosure within the MEMs structure which filter allows flow of the etchant, but not the particles through the filter. The filter is opening by dissolving a photoresist barrier with a liquid solvent or a silicon barrier could be etched with a gaseous etchant to define an opening smaller than the particles.

The illustrated embodiment shows the fabrication of a MEMs structure on the substrate comprises fabricating a liquid chromatograph column.

The multiplicity of particles may be of such a type as to provide labeled microspheres to allow visualization and detection of the microspheres in the MEMs structure, magnetic microspheres, encapsulated microspheres having chemically specific polymer shells for selectively binding to predetermined molecules, expansive microspheres or electrokinetic microspheres for providing a pressure.

The invention is also broadly defined to include a method for fabricating a thick film using thin film material comprising the steps of mixing a multiplicity of particles into the thin film material to establish a predetermined viscosity of the mixture greater than the thin film material without the particles by varying the concentration of the particles in the mixture, and disposing the mixture onto a substrate to form a thick film. The mixture is degassed prior to disposing the mixture on the substrate to remove bubbles.

In summary what is disclosed is an, inexpensive, batch process for integration of microparticles into MEMS. This process is suitable for all kinds of microparticles and for a wide range of particle sizes. With this process, introduction and localization of particles becomes much less complicated, and is thus attractive for many applications. Using this technique, micro-channels filled with conventional HPLC column beads can be fabricated and used as on-chip separation columns in micro total analysis systems ($\mu$TAS). Other various microparticles with various applications have also been addressed. Moreover, it is found that adding particles to a spin-coating material can substantially increase the resulting film thickness, which enables many thick-film applications of thin-film materials.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

Figure 1A:
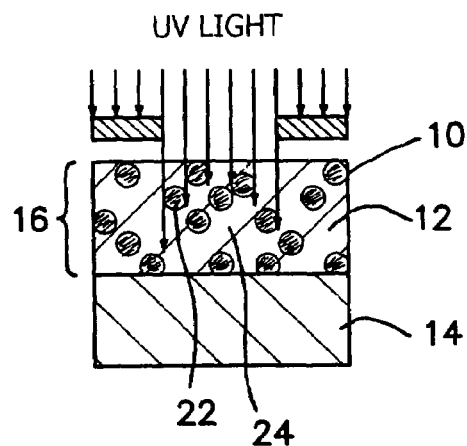
FIGS. 1a–1c are simplified side cross-sectional views of a particle embedded mixture being patterned and etched using photolithographic methods.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

The invention integrates microparticles or beads 10 on a chip or substrate 14 using micromachining technology. By introducing particles, such as microspheres, as an integral part of MEMS devices, great potential of growth in applications can be achieved.

As shown in FIGS. 1 and 2 particles 10 are firstly mixed with a sacrificial material 12 then the mixture is coated onto a wafer substrate 14. The mixture layer 16 is patterned and covered by structural materials by conventional methods. After processing on the structural layers according to conventional steps, the supporting media of the particles, i.e. the sacrificial material 12, is removed to leave only particles 10 inside the structures. On-chip micromachined filters 18 as shown in one example in FIGS. 3a–3e can be built as part of the MEMS process and are employed to keep the integrated particles at the places desired. The capturing or retaining MEMs structure need not be a filter body, but may be any topology capable of restricting or retaining the particles to a predefine area or microstructure.

This process is inexpensive and works for a wide range of particle sizes. In addition, a unique feature of the mixing process is that the resulting spin-coated sacrificial film thickness can be increased dramatically by adding enough particles to increase the effective viscosity of the mixture. Hence, introducing particles 10 can allow many thin film materials to extended for use in thick film applications.

To demonstrate the process, in the illustrated embodiment beads-packed channels used as separation columns 20 are fabricated as discussed below in connection with FIGS. 3a–3e. Separation columns 20 are integrated to make completely on-chip chromatography systems, such as high performance liquid chromatography (HPLC) systems. Beads used in conventional HPLC columns are integrated into an on-chip separation microchannel 20. By integration, the design and fabrication of completely miniaturized HPLC system is greatly simplified. Moreover, the internal compatibility problem is solved. An HPLC column is shown as an example, and it is to be expressly understood that the invention can be integrated into the fabrication of any MEMs device now known or later devised.

Figure 1B:
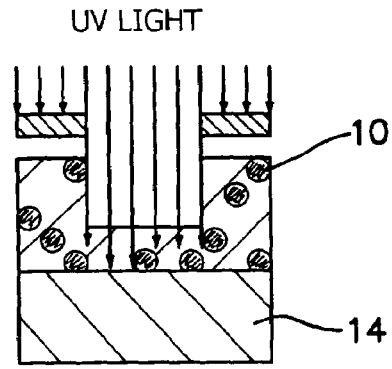

The process starts in FIG. 1a with mixing microparticles, such as microspheres 10, with a sacrificial material 12, such as photoresist. By measuring the weight and knowing the density of the microparticles 10, the total volume of the particles 10 and thus the volume mix ratio between the sacrificial material 12 and particles 10 can be determined. Then to remove the bubbles generated by mixing, the mixture 16 can be degassed by any degassing technique, such as use of a vacuum jar and centrifuge. After that, the mixture 16 is applied onto the wafer substrate 14 in FIG. 1a by standard spin coating or any other appropriate coating processes, such as squeegee.

The thickness of the spin-coated mixture layer 16 is controlled by the mix ratio, as well as spin speed and time. Thicker film is expected for more particles 10 in the mixture, since the effective viscosity increases with increasing particle contents in the mixture 16. It is found that by adding enough particles 10 to a spin-coating material 12, the thickness of the resulting film 16 can be increased substantially, thus enable many thin film materials to work as thick ones. Moreover, the coated film thickness can be further increased by multiple spin coatings.

Because the mixture layer 16 is usually thick, patterning can be done by multiple exposure-developing cycles, if necessary. Only increasing the exposure time is found to be much less effective than successive exposure-developing cycles, since the particles in the mixture 16 block UV light thus significantly reducing transparency as schematically depicted in FIG. 1a. Even if the top part of the mixture layer 22 is over-exposed, the bottom part 24 may still be under-exposed, because there is little light going through the particle-embedded mixture 16 and reaching the bottom 24. Therefore, the exposed top part 22 must be developed away to give enough light access to the lower parts 24 of the layer in a multiple step process schematically depicted in FIG. 1(b).

Figure 1C:
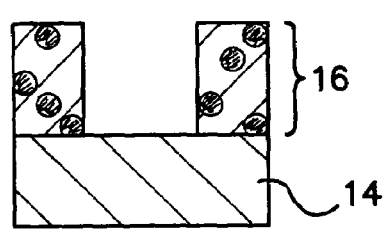

By exposing and developing for several times, the mixture layer 16 can be easily and completely patterned as schematically depicted in FIG. 1c. Ultrasonic cleaning can then be used to detach and remove any particles still sticking on the substrate 14.

Figure 2A:
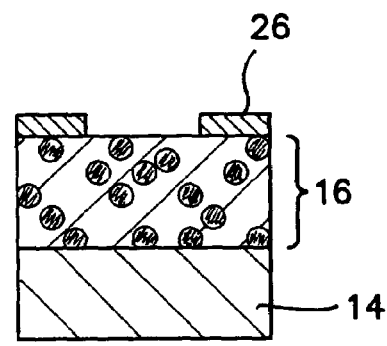
FIGS. 2a–2c are simplified side cross-sectional views of a particle embedded mixture being patterned and etched using chemical and other etching methods.
Figure 2B:
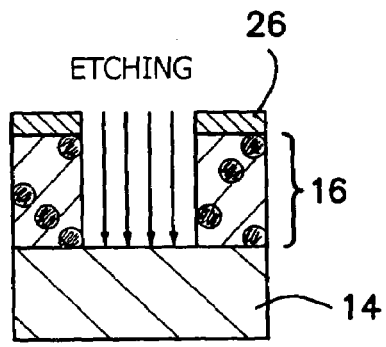
Figure 2C:
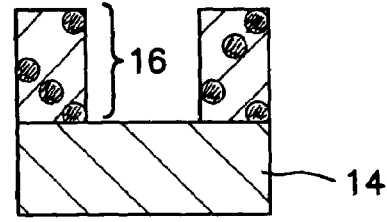

The patterning can also be done by chemical or other types of etching when the material cannot be patterned directly by photolithography, or if the number of exposure-developing cycles is too large to make the process practical as schematically depicted in FIGS. 2a–2c. With a patterned mask material 26 on top of the mixture 16, the mixture 16 can be patterned by wet or dry etching processes, such as reactive ion etching (RIE) and plasma etching as shown in FIG. 2b.

After patterning, the sacrificial layer 12 is covered by structural materials, such as conformal-coated Parylene. Processing can be done in these structural layers prior to opening access to the sacrificial layer 12, which is then removed by corresponding etchants or solvents, such as photoresist stripper or acetone when photoresist is used as the sacrificial material 12. The particles 10 are kept inside the structures by on-chip filters 18, which usually are designed to restrict one dimension of the flow channel, such as height, to prevent particles 10 from leaving or entering the fluidic system, in other words some kind of a box or dam is built around particles 10.

With this easy, inexpensive method to integrate and localize microspheres 10 on chip, there can be numerous applications, considering the various applications that microspheres 10 already have off-chip, especially in biological and biomedical areas, and the new opportunities that the integration creates on-chip. Some examples are provided below.

1. Liquid Chromatography Column

Chromatographic packing beads can be integrated to make on-chip separation columns 20 which ease the building of miniaturized total analysis systems ($\mu$TAS). A sample fabrication is done using the process described above. This device is proposed to make an integrated separation column 20 as part of a complete on-chip HPLC system. Beads 10 used here are support materials in conventional HPLC columns and these beads (from Vydac) have 5 $\mu$m in diameter and are coated with carbon-18 alkyl groups. Beads 10 are sealed by filters 18 at two ends of the micro-channels made of Parylene. The channels 20 are 60 $\mu$m wide, 20 $\mu$m high and 0.5 cm long. The fabrication process shown in FIGS. 3a–3e starts with the step of coating the substrate 14 with A-174 adhesion promoter and then 1 $\mu$m Parylene 28 to improve adhesion of subsequent Parylene layers to the substrate. Photoresist 30 with 2.5 $\mu$m thickness is applied and patterned by conventional means. The second layer 32 of Parylene is deposited without applying adhesion promoter and patterned with oxygen plasma to form the filter parts 34. Beads 10 are mixed with photoresist AZ9260 from Clariant and the mixture 16 is degassed in a vacuum oven.

Figure 3A:
FIGS. 3a–3e are simplified side cross-sectional views of the fabrication of a flow separation microchannel using a particle embedded mixture patterned as shown in FIGS. 1 or 2.
Figure 3B:
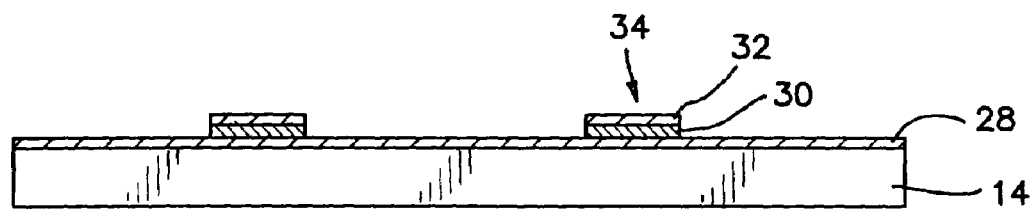
Figure 3C:
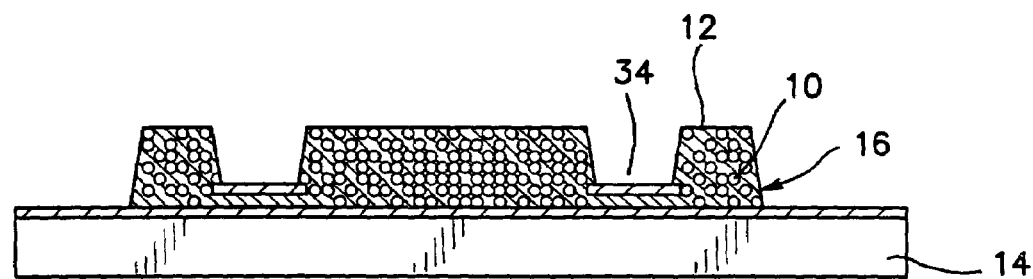
Figure 3D:
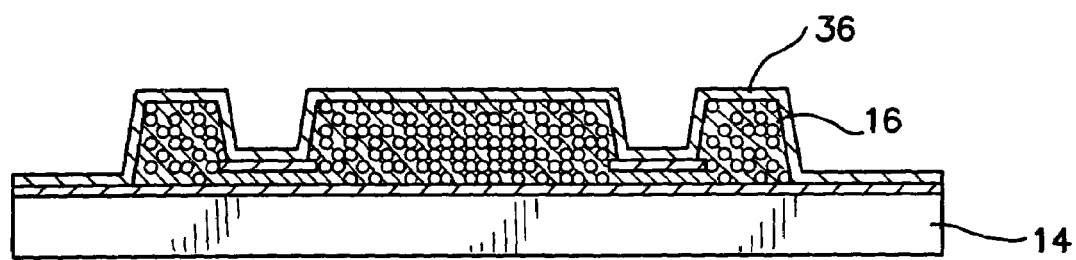
Figure 3E:
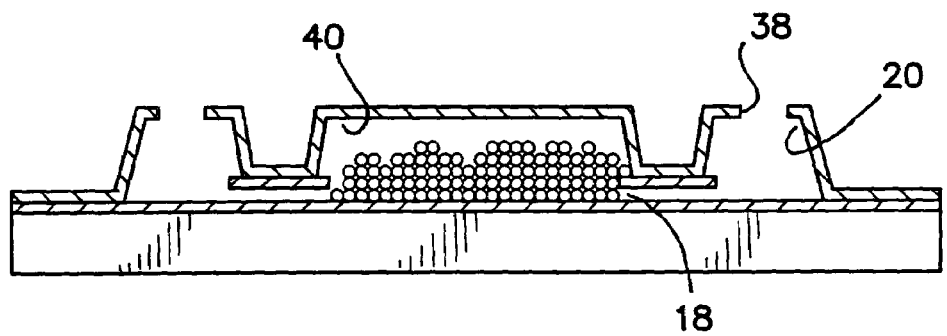

Then the mixture 16 is spin-coated and patterned by two exposure-developing cycles, using GCA 10x reduction Stepper and AZ400K developer from Clariant to obtain a pattern such as shown in FIG. 3c. The wafer 14 is further cleaned in an ultrasonic bath to remove beads 10 sticking on the wafer surface. Another 3 $\mu$m Parylene layer 36 is then applied as shown in FIG. 3d and patterned with oxygen plasma to form all the fluidic structures and to open access holes 38 to the sacrificial photoresist 12 as shown in FIG. 3e. The wafer 14 is diced and finally each die can be released individually by immersing in acetone or photoresist stripper. The beads 10 inside the channel 40 pack automatically when there is a flow through the channel 40.

Photoresist is simply used here for the 2.5 $\mu$m high filter part 34 in order to seal the 5 $\mu$m beads. For even smaller beads, 1 $\mu$m for instance, polysilicon or sputtered amorphous silicon can be utilized as a sacrificial material 12 and later removed by $BrF_3$ or $XeF_2$ gas dry etching.

Figure 4A:
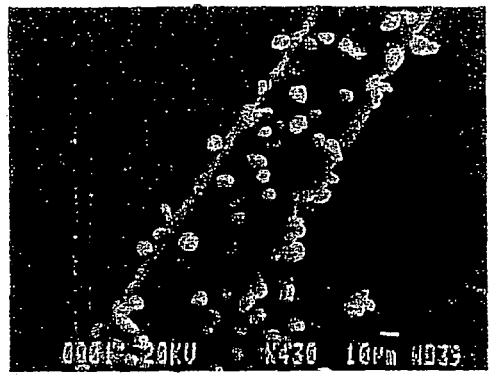
FIGS. 4a and 4b are scanning electron photographs showing the embedding of microspheres in sacrificial materials at two different bead concentrations.
Figure 4B:
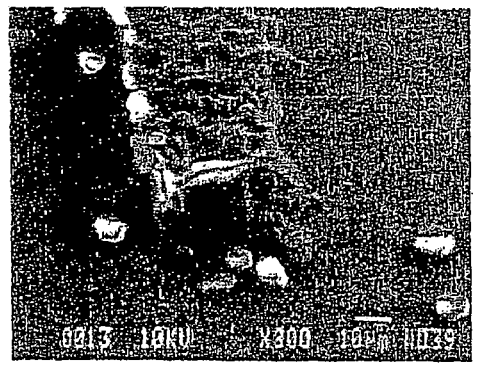

Fixing all other spinning conditions, more beads content in the mixture leads to thicker spin-coated film. FIGS. 4a and 4b provide a photographic comparison. Two wafers have been spin-coated with doped photoresists with a layer having a beads contents which 3.5 times thicker in FIG. 4b than that in FIG. 4a. The diameter of the beads 10 in both cases is 5 $\mu$m. After patterning, the measured thicknesses of the doped resist layers are 12 um for FIG. 4a and 45 $\mu$m for FIG. 4b, which shows more beads result in a thicker film. Moreover, thinner film in FIG. 4a has a lot of beads sticking out on the resist surface, while thicker film in FIG. 4b has most beads buried under the surface, which can be seen from the SEM pictures in FIGS. 4a and 4b. This means the spin-coated mixture film has to be thick enough to keep most beads inside the sacrificial material 12.

Figure 5A:
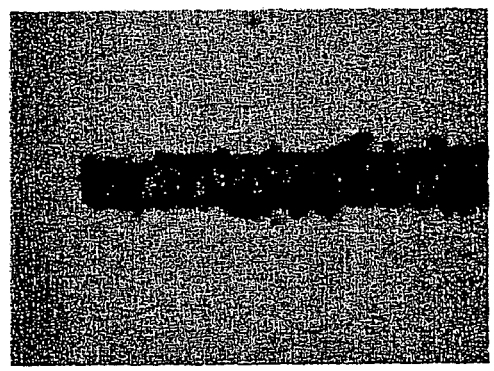
FIGS. 5a and 5b are scanning electron photographs showing the removal of the sacrificial material for a 3 $\mu$m and 1 $\mu$m Parylene C coating respectively carrying microspheres.
Figure 5B:
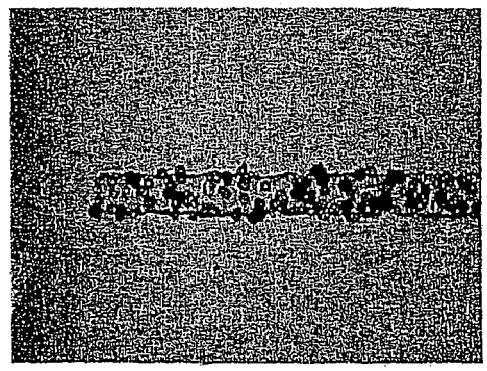

The SEM pictures in FIGS. 4a and 4b also show the roughness of the spin-coated film surfaces. To study how thick the Parylene coating on these rough surfaces has to be, in order to be leak-free, chips with doped photoresist patterns are covered with Parylene C "conformal" coating with different thicknesses. Then by soaking the coated chips in acetone, those with pinholes can be identified. It is found that 3 $\mu$m Parylene C can provide a pinhole-free coating for this application, while some of the 2 $\mu$m and all of the 1 $\mu$m coated samples are quickly attacked by acetone, as shown in the comparison of FIGS. 5a and 5b. FIG. 5b also shows that a Parylene channel with photoresist and beads mixture inside can be released by immersing in acetone leaving only beads inside the channel.

All kinds of microspheres can be integrated to have various applications. Fluorescent and dyed microspheres are especially useful for micro-flow visualization and detection. Magnetic microspheres can be actuated by on-chip magnetic fields thus can have many application, such as micro-mixer and chemical reagents transportation. Encapsulated magnetic microspheres with polymer shells can be used for on-chip DNA amplification by polymerase chain reaction (PCR). Microspheres with specific surface characteristics facilitate binding to proteins or antibodies and manipulation of these microspheres transports the proteins or antibodies to the locations desired. Also, arrays of localized microspheres with special coatings are demonstrated for "e-tongue", which analyzes complex fluids containing a variety of important classes of analytes, including acids, bases, metal cations, metabolic cofactors, and antibody reagents. Expandable microspheres can be used for liquid handling, such as one-time micro-pumps and micro-valves. Moreover, high pressures can be generated electrokinetically in beads packed micro-channels.

One unique feature of the mixing and spin-coating process presented here is that the spin-coated film thickness increases dramatically when doped with particles compared to no doping, which is due to the increased effective viscosity of the doped material. In addition, the thickness can be further increased by multiple spin coating steps. Thus, thin film materials can have thick film applications by doping particles.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself. The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination. Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements. The claims are thus to be understood to include what is specifically illustrated and described above, what is conceptionally equivalent, what can be obviously substituted and also what essentially incorporates the essential idea of the invention.

We claim:

1. A method for fabricating MEMs devices comprising:
   providing a mixture of a sacrificial material and a multiplicity of particles;
   disposing the mixture onto a substrate;
   fabricating a MEMs structure on the substrate including at least part of the mixture, so that at least some of the mixture is enclosed in the MEMs structure;
   removing the sacrificial material; and
   leaving at least some of the multiplicity of particles substantially free and enclosed in the MEMs structure.

2. The method of claim 1 where fabricating a MEMs structure on the substrate including at least part of the mixture comprises photolithographically patterning the mixture.

3. The method of claim 1 where fabricating a MEMs structure on the substrate including at least part of the mixture comprises patterning the mixture by etching the mixture.

4. The method of claim 1 where providing a mixture of a sacrificial material and a multiplicity of particles comprises providing a mixture of variable viscosity, wherein the viscosity is determined by particle concentration.

5. The method of claim 1 where providing a mixture of a sacrificial material and a multiplicity of particles comprises providing particles in a soluble material.

6. The method of claim 5 where providing a mixture of a sacrificial material and a multiplicity of particles comprises providing particles in photoresist.

7. The method of claim 1 where disposing the mixture onto a substrate comprises spin coating the mixture onto the substrate.

8. The method of claim 7 where spin coating the mixture onto the substrate further comprises controlling the thickness of the coating by varying the concentration of particles in the mixture.

9. The method of claim 1 where fabricating a MEMs structure on the substrate including at least part of the mixture comprises repeatedly photolithographically exposing and etching the mixture.

10. The method of claim 1 where fabricating a MEMs structure on the substrate including at least part of the mixture comprises reactive ion etching the mixture.

11. The method of claim 1 where fabricating a MEMs structure on the substrate including at least part of the mixture comprises plasma etching the mixture.

12. The method of claim 1 where removing the sacrificial material comprises defining openings in the MEMs structure to allow entry of an etchant of the sacrificial material and opening at least one filter into an enclosure within the MEMs structure which filter allows flow of the etchant, but not the particles through the filter.

13. The method of claim 12 where defining openings in the MEMs structure to allow entry of an etchant of the sacrificial material and opening at least one filter into an enclosure within the MEMs structure comprising dissolving photoresist with a liquid solvent.

14. The method of claim 12 where defining openings in the MEMs structure to allow entry of an etchant of the sacrificial material and opening at least one filter into an enclosure within the MEMs structure comprising etching the substrate with a gaseous etchant.

15. The method of claim 1 where fabricating a MEMs structure on the substrate comprises fabricating a liquid chromatograph separation column.

16. The method of claim 1 where providing a mixture of a sacrificial material and a multiplicity of particles provides label particles to allow visualization and detection of the particles in the MEMs structure.

17. The method of claim 1 where providing a mixture of a sacrificial material and a multiplicity of particles provides magnetic particles.

18. The method of claim 1 where providing a mixture of a sacrificial material and a multiplicity of particles provides encapsulated particles having chemically specific polymer shells for selectively binding to predetermined molecules.

19. The method of claim 1 where providing a mixture of a sacrificial material and a multiplicity of particles provides expandable particles for providing an expansive force.

20. The method of claim 1 where providing a mixture of a sacrificial material and a multiplicity of particles provides electrokinetic particles for providing a pressure.

21. The method of claim 1, wherein the particles are microparticles or nanoparticles.

22. The method of claim 1, wherein the particles are microparticles.

23. The method of claim 1, wherein the particles are nanoparticles.

24. The method of claim 1, wherein the particles are microspheres or microbeads.

25. The method of claim 1, wherein the particles are microparticles of HPLC support material.

* * * * *